(12) United States Patent
Liou et al.

(10) Patent No.: US 8,088,932 B2
(45) Date of Patent: Jan. 3, 2012

(54) PENTAARYLDIAMINE-CONTAINING BISMALEIMIDE COMPOUND AND METHOD OF PRODUCING THE COMPOUND

(75) Inventors: Guey-Sheng Liou, Hsinchu (TW); Cha-Wen Chang, Hsinchu (TW); Hung-Ju Yen, Hsinchu (TW); Jing-Pin Pan, Hsinchu (TW); Chang-Rung Yang, Hsinchu (TW); Tsung-Hsiung Wang, Hsinchu (TW); Jung-Mu Hsu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 204 days.

(21) Appl. No.: 12/427,077

(22) Filed: Apr. 21, 2009

(65) Prior Publication Data
US 2010/0168442 A1   Jul. 1, 2010

(30) Foreign Application Priority Data

Dec. 25, 2008   (TW) ................................ 97150580 A

(51) Int. Cl.
*C07D 207/452*   (2006.01)
(52) U.S. Cl. ........................................ 548/521; 548/522
(58) Field of Classification Search .................. 548/521, 548/522
See application file for complete search history.

(56) References Cited

OTHER PUBLICATIONS

Takahira et al. (STN Abstract of JP 04020518).*
Soo-Young Park et al., "Preparation and Properties of a Poly(2-cyano-1,4-phenylene terephthalamide)/Layered Silicate Nanocomposite", Journal of Applied Polymer Science, 2006, pp. 640-645, vol. 102.
Frank W. Mercer et al., "Synthesis and Properties of Fluorinated Polyimides and Fluorinated Poly(imide amide)s Containing Pendent Cyano Groups", Polymer International, 1994, pp. 399-407, vol. 33, No. 4.
G.P. Cao et al., "Synthesis and thermal properties of the thermosetting resin based on cyano functionalized benzoxazine", Polymer Degradation and Stability, 2008, pp. 739-744, vol. 93.

* cited by examiner

*Primary Examiner* — Robert Havlin
(74) *Attorney, Agent, or Firm* — Rabin & Berdo, P.C.

(57) ABSTRACT

Provided is a pentaaryldiamine-containing bismaleimide compound of Formula (I):

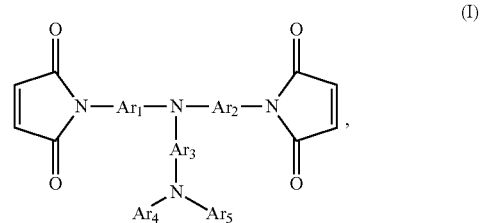

wherein $Ar_1$ to $Ar_5$ are independently $C_6$-$C_{12}$ aryl; and $Ar_4$ and $Ar_5$ are optionally substituted by one or more substitutent(s) selected from the group consisting of $C_1$-$C_6$ alkyl, $C_1$-$C_6$ alkoxy, and cyano. The compound of Formula (I) is obtained by a method including the steps of reacting a diamine with maleic anhydride in a solvent to form an amic acid, and cyclodehydrating the amic acid in the presence of a catalyst and a dehydrating agent. The compound of Formula (I) has a nonlinear and asymmetric structure, is amorphous, and is readily soluble in a variety of organic solvents so that the toughness of the product made there from can be improved and processing of the compound can be simplified.

14 Claims, 7 Drawing Sheets
(1 of 7 Drawing Sheet(s) Filed in Color)

PENTAARYLDIAMINE-CONTAINING BISMALEIMIDE COMPOUND AND METHOD OF PRODUCING THE COMPOUND

FIELD OF THE INVENTION

The present invention relates to bismaleimide compounds and producing methods thereof. More specifically, the present invention relates to pentaaryldiamine-containing bismaleimide compounds and producing methods thereof.

BACKGROUND OF THE INVENTION

Polyimide compounds, due to their high thermostability and excellent insulating property, mechanical strength and resistance to chemical corrosion, are applicable in various electronic materials, such as thermostable heat-resistant circuit boards, high-temperature binders, copper clad laminates, adhesive materials of coating copper foil and the like.

However, most imide compounds are soluble only in aprotic polar solvents with high boiling point, such as N-methyl-2-pyrrolidone, N,N-dimethylacetamide and etc, but are insoluble in organic solvents with low boiling point due to their imide structure. It is very difficult to remove aprotic polar solvents with high boiling point from the other components; therefore these solvents are usually retained in final products, resulting in increased difficulty in future processing of the products. In another aspect, since the imide compounds are less soluble in common organic solvents with low boiling point, they are difficult to be used in combination with other compounds or polymers, which highly restricts their application in industry.

It was also reported by Soo-Young Park; Seung-Woo Lee and Tae-Jin Oh (J. Appl. Polym. Sci., 2006, 102, 640) that process control of a polymer compound can be improved and simplified by introducing a cyano group (—CN) on the phenylene rings thereto to increase its solubility in polar organic solvents. Frank W. Mercer; Martin T. Mckenzie; and Maria Bruma (Burkhard. Schulz. Polym. International, 1993, 33, 4, 399) disclosed that a polymer compound may have increased glass transition temperature, dielectric constant and changed electrochemical properties when a cyano group (—CN) is introduced on the phenylene rings thereto to provide it strong electron-withdrawing property. It was also disclosed by G. P. Cao; W. J. Chen and X. B. Liu (Polymer Degradation and Stability, 2008, 93, 739) that a polymeric material may have improved thermo-oxidative resistance, flame retardancy, oxidative stability, char yield, and processability by introduction of cyano (—CN) groups on the phenylene ring thereto.

However, it is still desirable to develop a modified imide compound which has excellent solubility in common solvents, including those with low boiling points, and can impart higher toughness to the products made therefrom, so as to improve its applicability in industry.

SUMMARY OF THE INVENTION

In some of the embodiments, the present invention provides a pentaaryldiamine-containing bismaleimide compound of Formula (I):

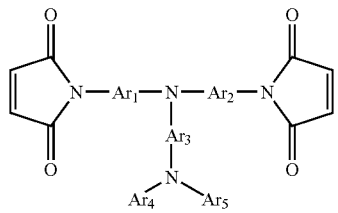

wherein $Ar_1$, $Ar_2$, $Ar_3$, $Ar_4$ and $Ar_5$ are independently $C_6$-$C_{12}$ aryl, and $Ar_4$ and $Ar_5$ may be optionally substituted.

Preferably, $Ar_4$ and $Ar_5$ may be independently substituted by one or more substitutent(s) selected from a group consisting of $C_1$-$C_6$ alkyl, $C_1$-$C_6$ alkoxy, $C_1$-$C_6$ alkylamino, di-$C_1$-$C_6$ alkylamino, carboxyl, amino, nitro, cyano and halogen.

Preferably, the aryl group is a phenyl group.

Preferably, the pentaaryldiamine-containing bismaleimide compound is N,N-bis(4-maleimidophenyl)-N',N'-bis(4-cyanophenyl)-1,4-phenylenediamine.

In some of the embodiments, the present invention provides a method for producing the above-defined pentaaryldiamine-containing bismaleimide compound of Formula (I), wherein $Ar_1$, $Ar_2$, $Ar_3$, $Ar_4$ and $Ar_5$ are independently $C_6$-$C_{12}$ aryl; and $Ar_4$ and $Ar_5$ may be optionally substituted, comprising the following steps:

(A) reacting a diamine compound of Formula (II):

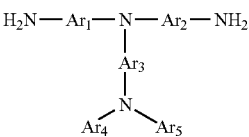

(wherein $Ar_1$, $Ar_2$, $Ar_3$, $Ar_4$ and $Ar_5$ are defined as above) with a maleic anhydride of Formula (III):

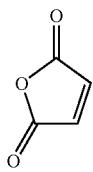

in a solvent to form a bismaleamic acid; and (B) cyclodehydrating the bismaleamic acid obtained in the step (A), in the presence of a catalyst and a dehydrating agent, to form the pentaaryldiamine-containing bismaleimide compound of Formula (I).

In some of the embodiments, the diamine compound used in the above method is N,N-bis(4-aminophenyl)-N',N'-bis(4-cyanophenyl)-,4-phenylenediamine.

In some of the embodiments, the present invention provides a pentaaryldiamine-containing bismaleimide polymer having a repeated unit of formula (IV):

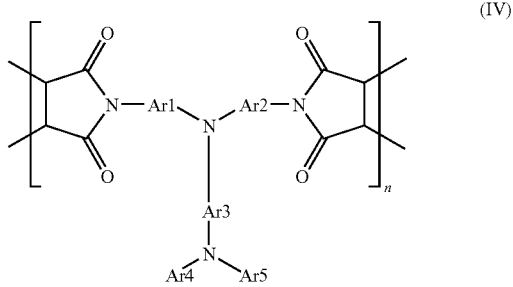

(IV)

wherein $Ar_1$, $Ar_2$, $Ar_3$, $Ar_4$ and $Ar_5$ are independently $C_6$-$C_{12}$ aryl, $Ar_4$ and $Ar_5$ may be optionally substituted, and n is the number of the repeated units of formula (IV) and is an integer of 1 to 15.

Preferably, the $C_6$-$C_{12}$ aryl group is a phenyl group. $Ar_4$ and $Ar_5$ may be independently substituted by one or more substitutent(s) selected from a group consisting of $C_1$-$C_6$ alkyl, $C_1$-$C_6$ alkoxy, $C_1$-$C_6$ alkylamino, di-$C_1$-$C_6$ alkylamino, carboxyl, amino, nitro, cyano and halogen. Preferably, $Ar_4$ and $Ar_5$ are independently substituted by a cyano group.

The pentaaryldiamine-containing bismaleimide compound, which has a nonlinear and asymmetric structure, has excellent solubility in common organic solvents with low boiling point; in addition, it is amorphous and hence can impart higher toughness to film products made therefrom. The compounds, which additionally have cyano substituents on the aromatic rings thereof, may have better thermo-oxidative resistance, flame retardancy, oxidative stability, char yield, and electron-withdrawing property (resulting in improved electrochemical properties), such that they can be subjected to various processing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
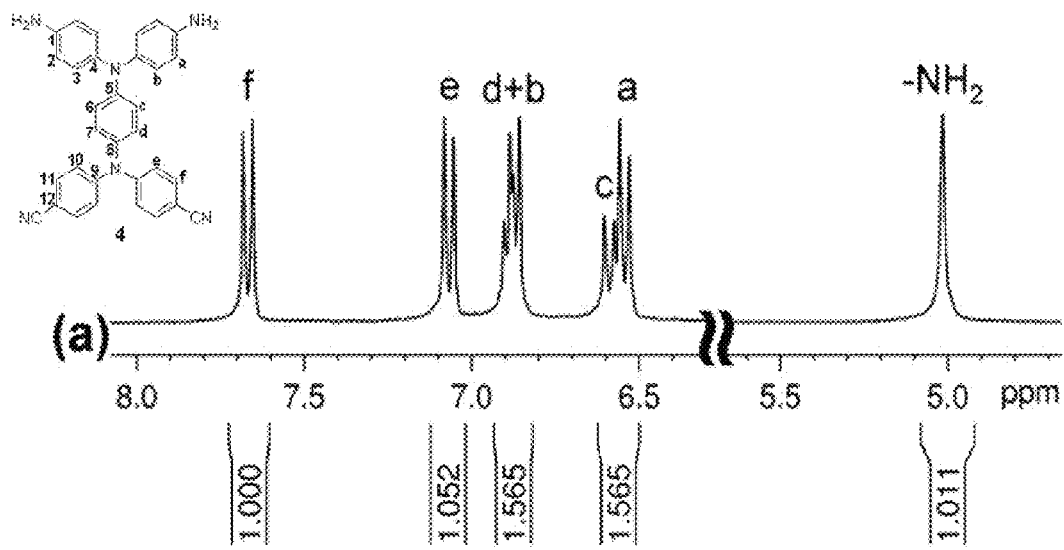
FIG. 1(a) is $^1$H-NMR spectrum of the diamine compound synthesized in Reference Example 1.
Figure 1B:
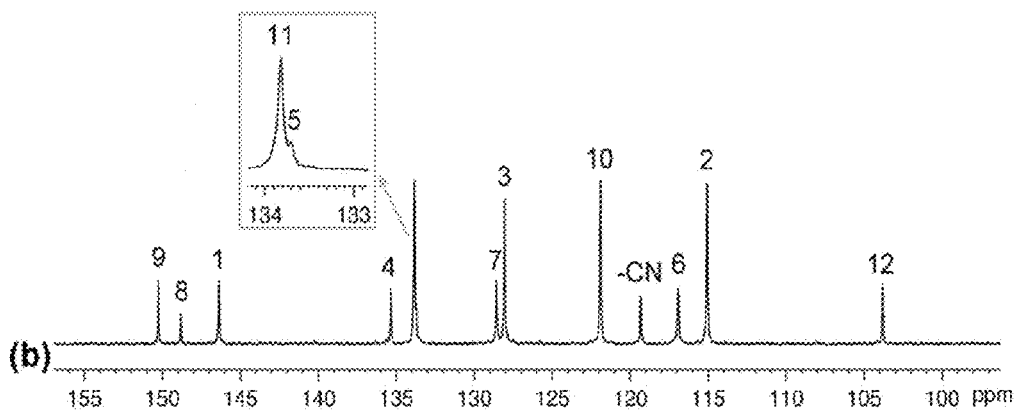
FIG. 1(b) is $^{13}$C-NMR spectrum of the diamine compound synthesized in Reference Example 1.
Figure 1C:
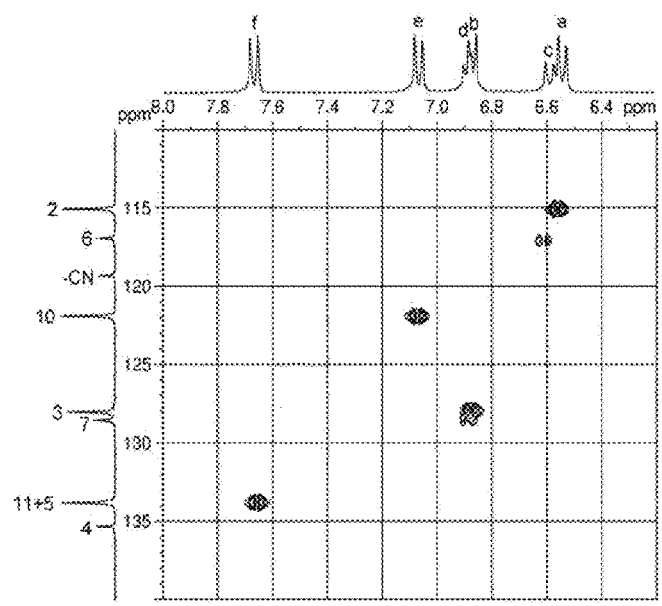
FIG. 1(c) is C—H HMQC spectrum of the diamine compound synthesized in Reference Example 1.
Figure 1D:
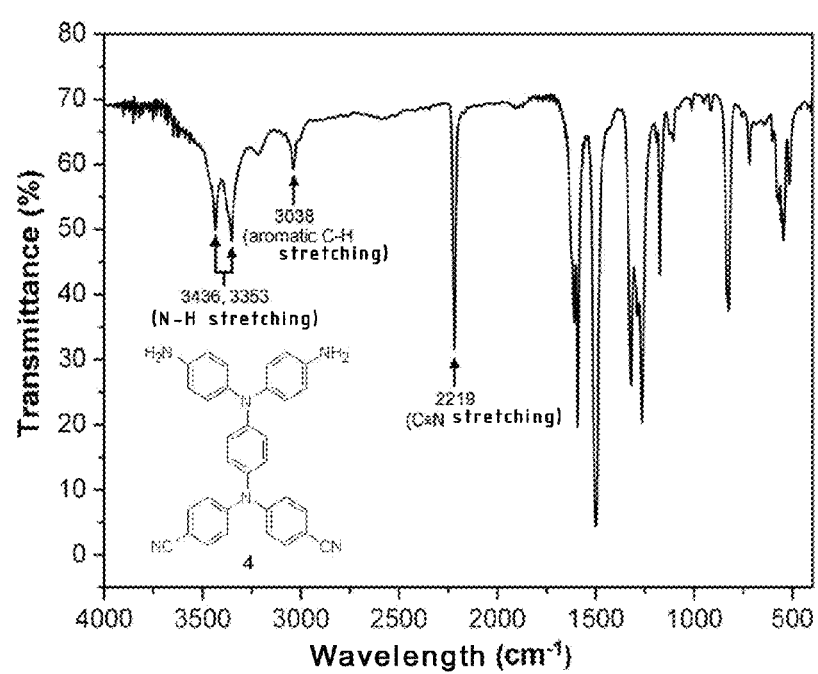
FIG. 1(d) is FT-IR spectrum of the diamine compound synthesized in Reference Example 1.
Figure 2A:
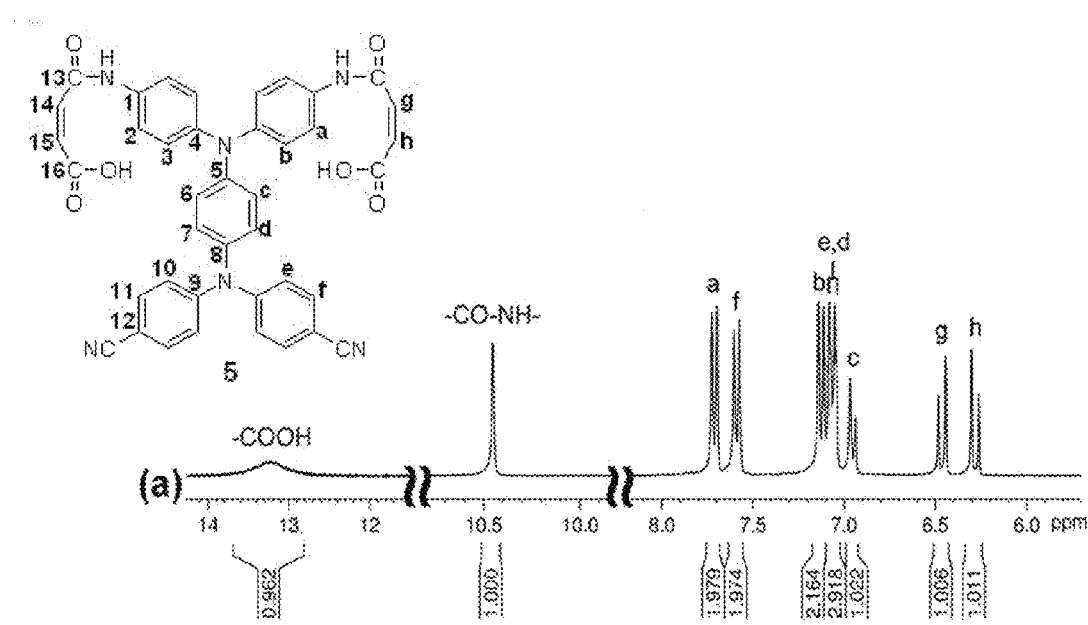
FIG. 2(a) is $^1$H-NMR spectrum of bismaleamic acid, which is an intermediate in production of pentaphenyldiamine-containing bismaleimide compound according to Example 1.
Figure 2B:
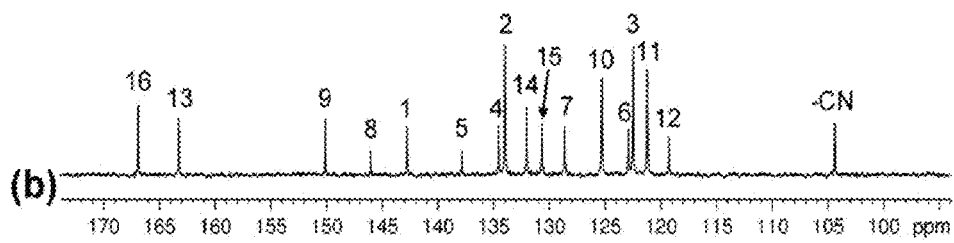
FIG. 2(b) is $^{13}$C-NMR spectrum of bismaleamic acid, which is an intermediate in production of pentaphenyldiamine-containing bismaleimide compound according to Example 1.
Figure 2C:
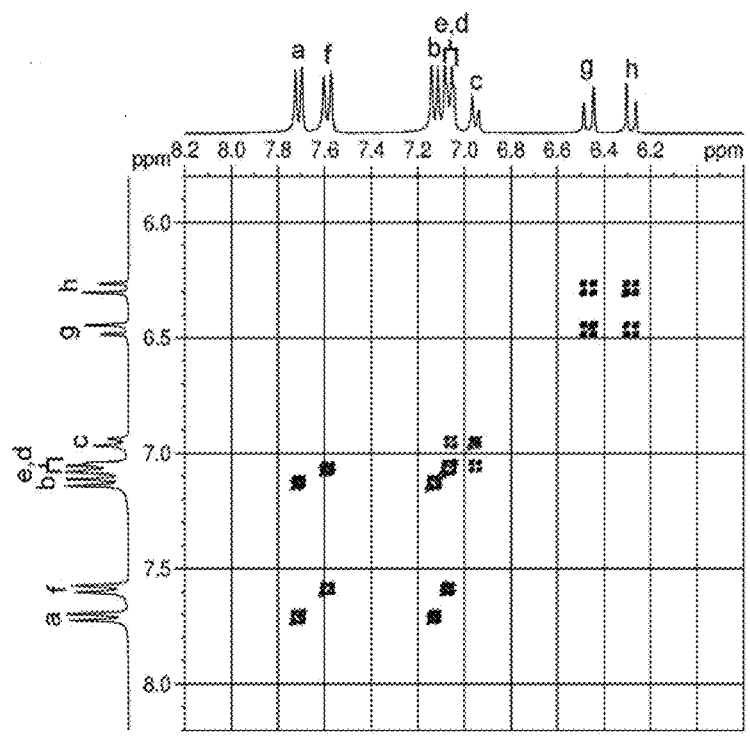
FIG. 2(c) is H—H COSY spectrum of bismaleamic acid, which is an intermediate in production of pentaphenyldiamine-containing bismaleimide compound according to Example 1.
Figure 2D:
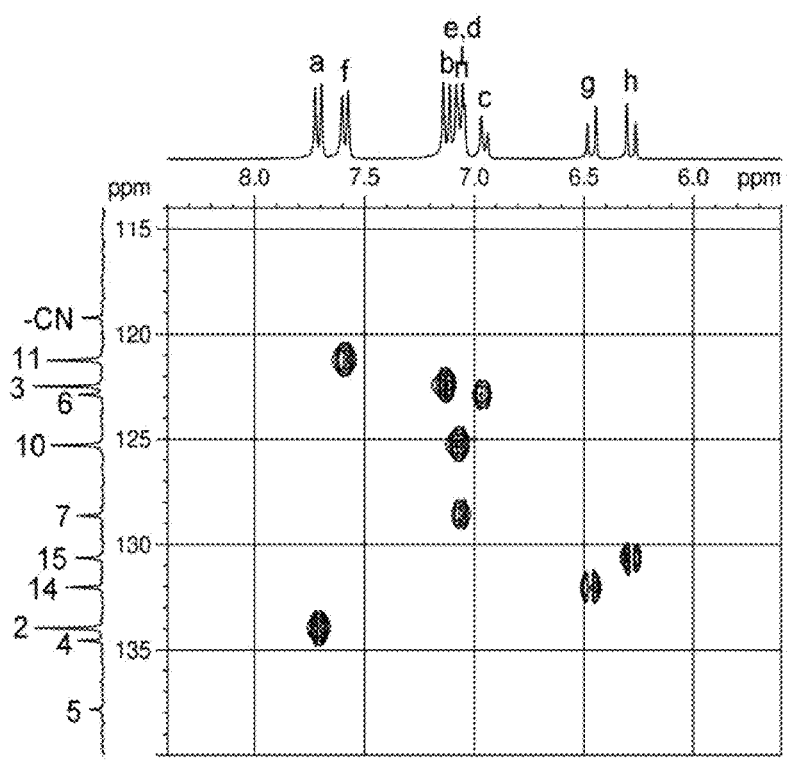
FIG. 2(d) is C—H HMQC spectrum of bismaleamic acid, which is an intermediate in production of the pentaphenyldiamine-containing bismaleimide compound according to Example 1.

The present invention can be fully understood by referring to the following detailed description and Examples. The description and Examples are merely intended to illustrate the present invention but should not be considered as a limitation to the present invention.

The invention relates to a pentaaryldiamine-containing bismaleimide compound, which has a nonlinear and asymmetric structure. The compound has excellent solubility in various organic solvents, including those with low boiling point; in addition, it is amorphous and hence can impart higher toughness to a film product made therefrom.

The compound which additionally has cyano substituents on the aromatic rings thereof may have the advantages of increased solubility, higher glass transfer (Tg) temperature, higher heat resistance, higher flame retardancy, higher oxidative stability, better electrochemical properties and the like.

Specifically, the invention provides a pentaaryldiamine-containing bismaleimide compound of Formula (I):

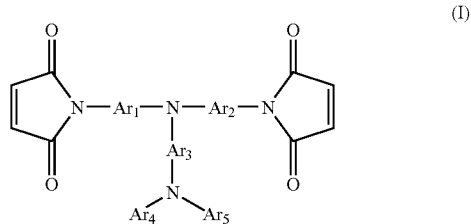

(I)

wherein $Ar_1$, $Ar_2$, $Ar_3$, $Ar_4$ and $Ar_5$ are independently $C_6$-$C_{12}$ aryl, and $Ar_4$ and $Ar_5$ may be optionally substituted. The $C_6$-$C_{12}$ aryl group is preferably a phenyl group. Preferably, $Ar_4$ and $Ar_5$ may be independently substituted by one or more substitutent(s) selected from a group consisting of $C_1$-$C_6$ alkyl, $C_1$-$C_6$ alkoxy, $C_1$-$C_6$ alkylamino, di-$C_1$-$C_6$ alkylamino, carboxyl, amino, nitro, cyano and halogen. Preferably, $Ar_4$ and $Ar_5$ are independently substituted by a cyano group.

In the other embodiments, the present invention also provides a method for producing a pentaaryldiamine-containing bismaleimide compound of Formula (I), comprising the following steps:

(A) reacting a diamine compound of Formula (II)

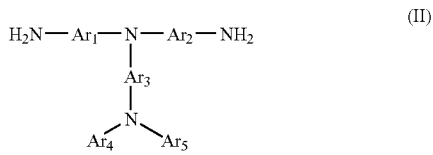

(wherein $Ar_1$, $Ar_2$, $Ar_3$, $Ar_4$ and $Ar_5$ are defined as above) with a maleic anhydride of Formula (III)

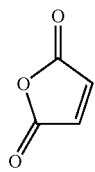

in a solvent to form a bismaleamic acid; and (B) cyclohydrating the bismaleamic acid obtained in the step (A) in the presence of a catalyst and a dehydrating agent, to form the pentaaryldiamine-containing bismaleimide compound of Formula (I). In some of the embodiments of the method for producing the pentaaryldiamine-containing bismaleimide compound of Formula (I), the diamine compound is N,N-bis(4-aminophenyl)-N',N'-bis(4-cyano phenyl)-1,4-phenylenediamine.

In the step (A), the diamine compound and maleic anhydride are mixed preferably at a molar ratio of 1:2.0 to 1:2.4, and more preferably at 1:2.19. The solvents suitable for use in the step (A) include, but are not limited to, ketones such as acetone, methyl ethyl ketone and methyl i-butyl ketone; and aprotic polar solvents such as N,N-dimethylformamide and N,N-dimethylacetamide.

The reaction for formation of bismaleamic acid in the step (A) is preferably carried out at a temperature of −10° C. to 40° C., and more preferably at −10° C. to 20° C. The bismaleamic acid may be cyclized at elevated temperature. The reaction is usually conducted at ambient temperature and ambient pressure. There is no limitation to the reaction time if it is sufficient for formation of the intermediate bismaleamic acid; however, the reaction time is preferably in the range of 6 to 24 hr, and more preferably in 6 to 12 hr. After the reaction is completed, the bismaleamic acid is isolated from the reaction mixture by filtration, then washed and purified, and used in the subsequent cyclodehydration step.

Cyclodehydration of the bismaleamic acid in the step (B) is carried out in a solvent, in the presence of a catalyst and a dehydrating agent, to form the pentaaryldiamine-containing bismaleimide compound of formula (I).

Examples of the catalyst suitable for use in the cyclodehydration include base catalysts such as sodium acetate and the like. Examples of the dehydrating agent suitable for use in the cyclodehydration include, but are not limited to acetic anhydride. Cyclodehydration of the bismaleamic acid is preferably carried out at 70° C. to 120° C., and more preferably at 80° C. to 100° C. for about 8 to 24 hr, preferably about 10 to 12 hr, and is quenched by adding ice water dropwise.

Moreover, the pentaaryldiamine-containing bismaleimide compound of the present invention can be subjected to polymerization in a solvent under heating in the presence of an initiator, to form a polymer with highly-branched structure and multiple double-bond reactive functional groups. Examples of the initiator suitable for use in the polymerization include, but are not limited to azobis(isobutyronitrile) (AIBN) and N-methylpyrrolidone (NMP). The polymerization is preferably carried out at 70° C. to 120° C., and more preferably at 80° C. to 100° C., and is quenched by adding methanol.

The features and effects of the present invention are further described by the following Examples, which are not restrictive of the scope of the present invention.

EXAMPLES

Reference Example 1

Synthesis N,N-bis(4-aminophenyl)-N',N'-bis(4-cyanophenyl)-1,4-phenylenediamine (a Diamine Compound)

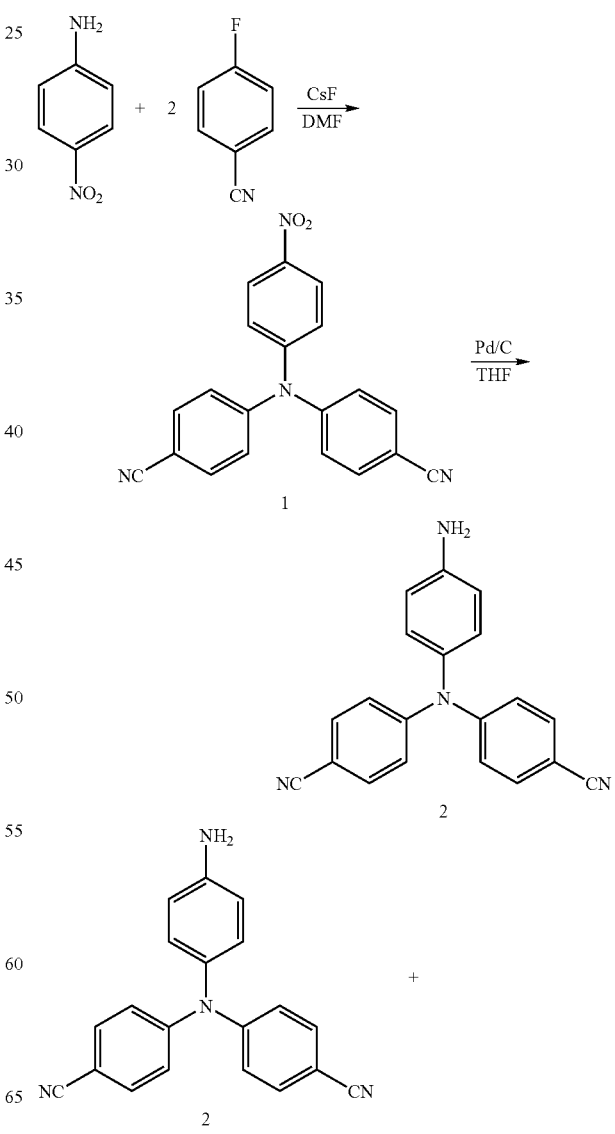

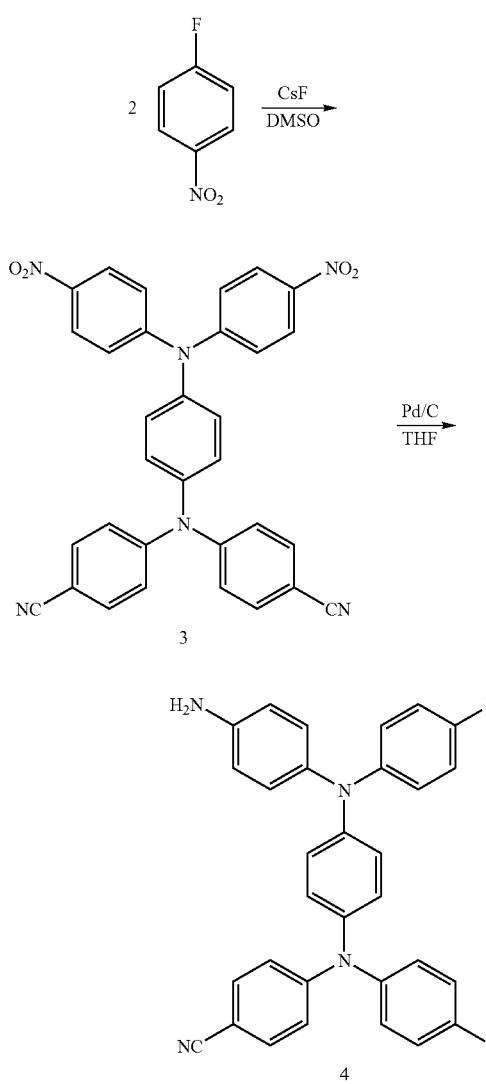

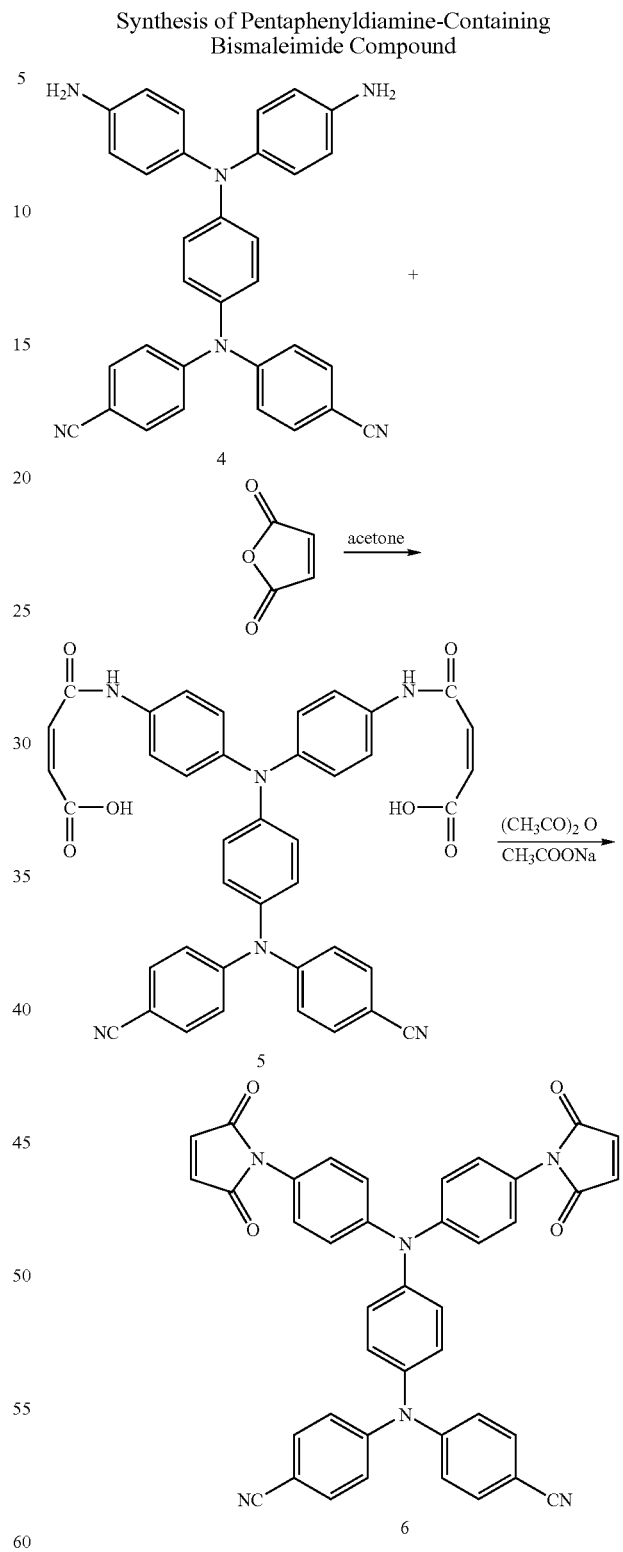

Example 1

Synthesis of Pentaphenyldiamine-Containing Bismaleimide Compound

A round-bottomed flask which had been flushed with nitrogen gas, 4-nitroaniline (8.29 g, 60 mmol) and 4-fluorobenzonitrile (15.30 g, 126 mmol) dissolved in N,N-dimethylformamide (250 mL) were charged thereto. Cesium fluoride was added as catalyst and the mixture was refluxed at 150° C. for 16 hr to obtain Compound 1 with a yield of 64%. Then, Compound 1 was dissolved in tetrahydrofuran and was hydrogenated in the presence of Pd/C to obtain Compound 2 with a yield of 88%. Compound 2 (310 g, 1 mol) and 1-nitro-4-fluorobenzene (280 g, 2 mol) were dissolved in dimethylsulfoxide(DMSO), cesium fluoride was added thereto as catalyst, and the mixture was refluxed at 150° C. for 24 hr to obtain Compound 3 as red solid with a yield of 71%. Compound 3 was dissolved in tetrahydrofuran and was hydrogenated in the presence of Pd/C to obtain Compound 4 (N,N-bis(4-aminophenyl)-N',N'-bis(4-cyanophenyl)-1,4-phenylenediamine) as yellow solid with a yield of 62%.

$^1$H—NMR, $^{13}$C—NMR, C—H HMQC and FT-IR spectra of Compound 4 are shown in FIG. 1(a), FIG. 1(b), FIG. 1(c) and FIG. 1(d) respectively. The melting point of Compound 4 is 216° C. to 218° C. as determined with a thermal analyzer.

A solution of maleic anhydride (1.05 g, 10.71 mmol) in acetone (10 mL) was charged into a 3-necked round-bottomed flask (250 mL) equipped with a feed tube, which had been flushed by nitrogen gas. Then, a solution of Compound 4 (2.41 g, 4.89 mmol) obtained from the Reference Example 1 in acetone (40 mL) was dropped into the round-bottomed flask slowly through the feed tube. The mixture was stirred at −5° C. for 12 hr. The insoluble solid was collected by filtration after the reaction was completed, and the filter cake was washed with acetone to obtain Compound 5 as red solid with a yield of 96% (3.23 g). $^1$H—NMR, $^{13}$C—NMR, H—H COSY and C—H HMQC of Compound 5 are shown in FIG. 2(a), FIG. 2(b), FIG. 2(c) and FIG. 2(d), respectively.

Figure 3A:
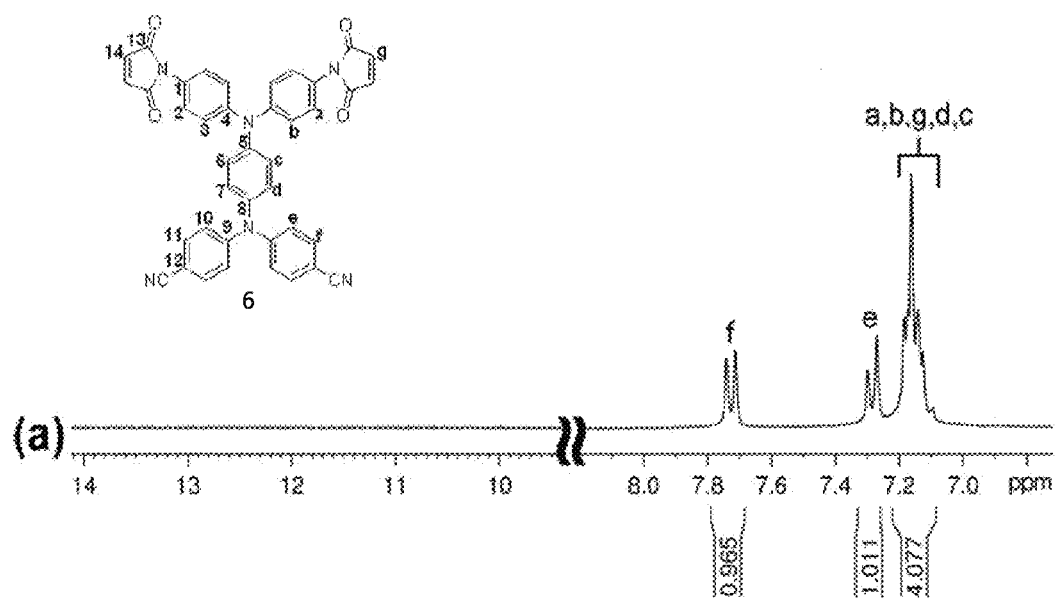
FIG. 3(a) is $^1$H-NMR spectrum of the pentaphenyldiamine-containing bismaleimide compound obtained in Example 1.
Figure 3B:
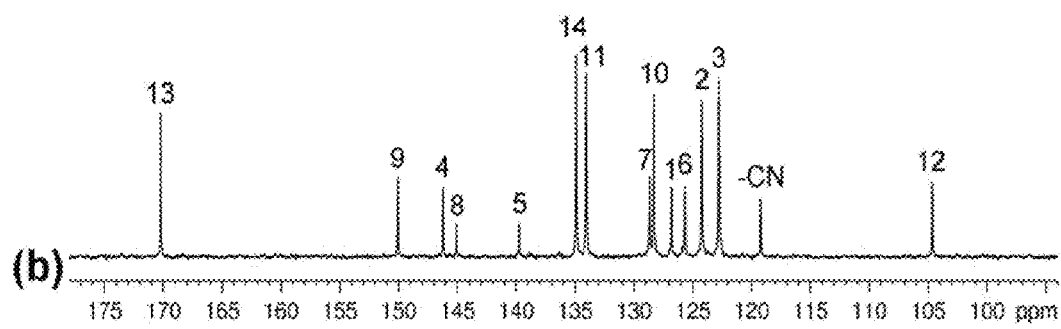
FIG. 3(b) is $^{13}$C-NMR spectrum of the pentaphenyldiamine-containing bismaleimide compound obtained in Example 1.
Figure 3C:
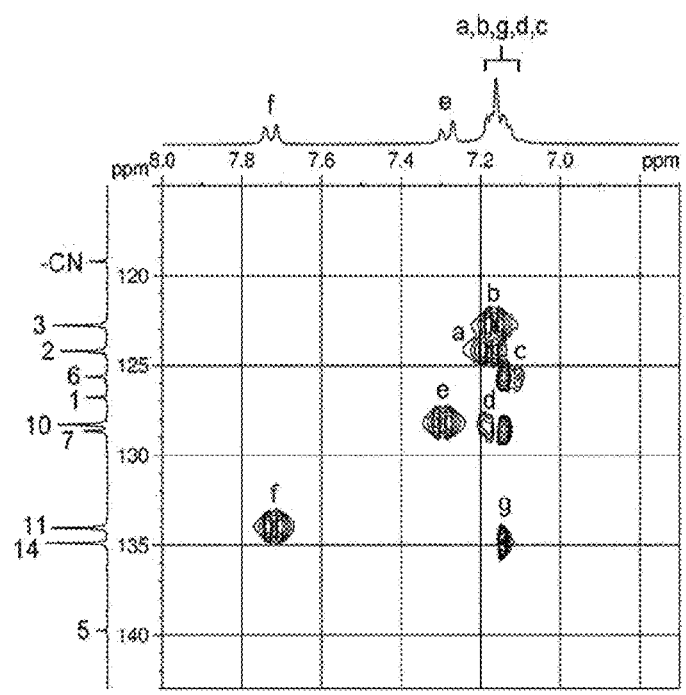
FIG. 3(c) is C—H HMQC spectrum of the pentaphenyldiamine-containing bismaleimide compound obtained in Example 1.
Figure 3D:
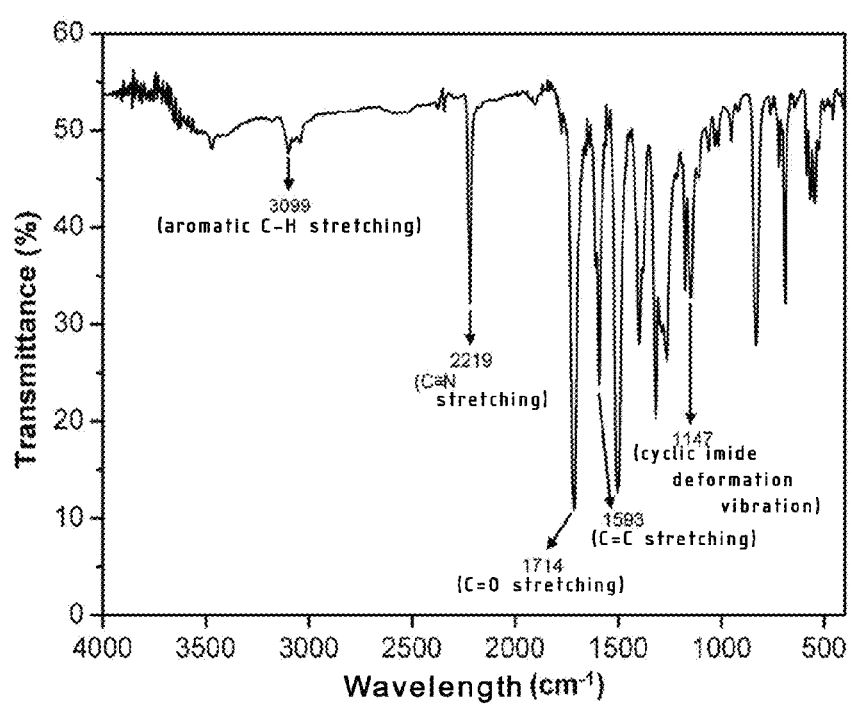
FIG. 3(d) is FT-IR spectrum of the pentaphenyldiamine-containing bismaleimide compound obtained in Example 1.
Figure 3E:
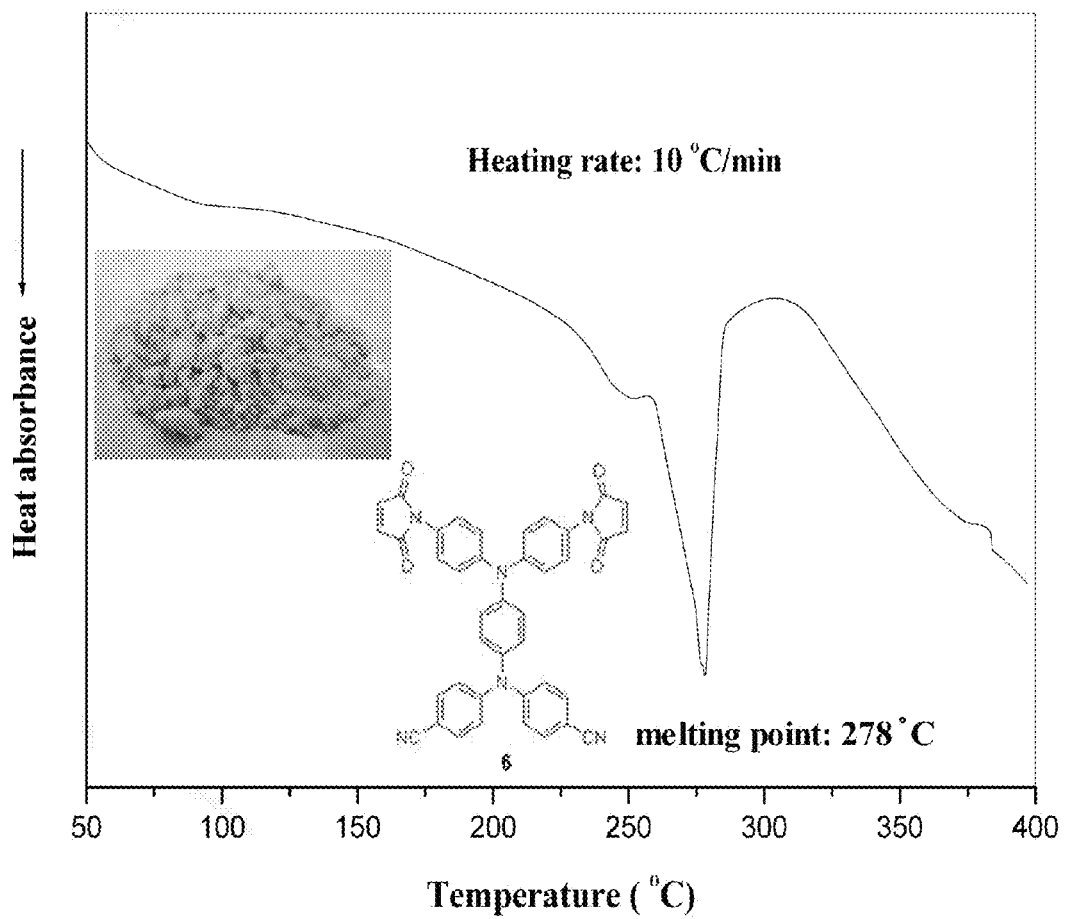
FIG. 3(e) is a graph showing the result of DSC analysis for the pentaphenyldiamine-containing bismaleimide compound obtained in Example 1, together with a photograph showing the appearance of the compound.

A 3-necked round-bottomed flask (250 mL) equipped with a feed tube was flushed with nitrogen gas and was placed in an oil bath. A solution of Compound 5 (3.00 g, 4.36 mmol) in acetone (30 mL) and anhydrous sodium acetate (0.24 g, 2.80 mmol) were charged into the 3-necked round-bottomed flask. Acetic anhydride (3.26 g, 31.94 mmol) was added dropwise through the feed tube. The mixture was heated to 80° C. slowly, then, was refluxed under stirring for 10 hr. After washing and crystallization, a yellow powder (its appearance can be seen in FIG. 3(e)) was obtained with a yield of 67% (1.90 g), which was identified to be Compound 6, i.e. N,N-bis(4-maleimidophenyl)-N',N'-bis(4-cyanophenyl)-1,4-phenylenediamine, by $^1$H-NMR, $^{13}$C-NMR, C—H HMQC and FT-IR analysis (referring to FIG. 3(a), FIG. 3(b), FIG. 3(c) and FIG. 3(d) respectively). The melting point of Compound 6 is 278° C. as determined with a thermal analyzer.

Example 2

Synthesis of Polymer from Pentaphenyldiamine-Containing Bismaleimide

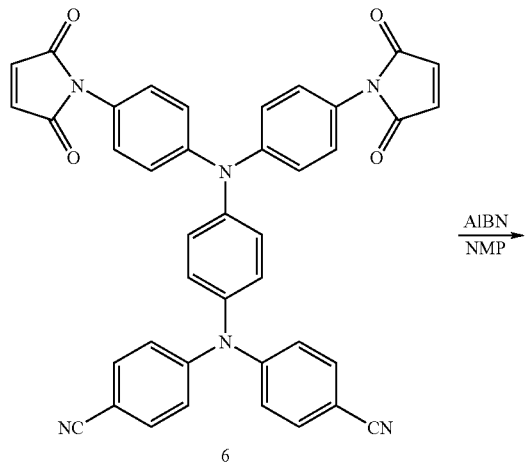

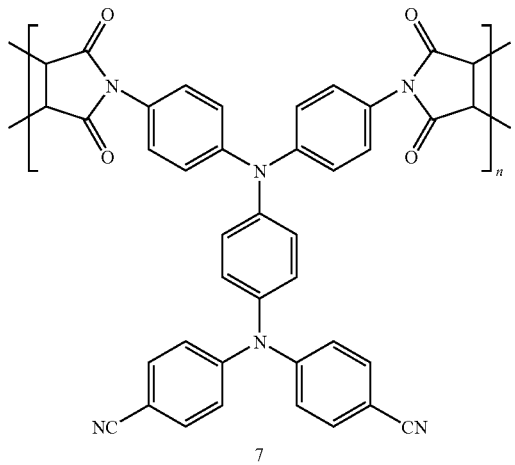

7

A 3-necked round-bottomed flask (100 mL) was flushed with nitrogen gas and was placed in a tank. A solution (5 mL) of Compound 6 (0.54 g, 0.83 mmol) obtained in Example 1 in N-methylpyrrolidone, and AIBN (0.68 g, 4.13 mmol) were directly charged into the 3-necked round-bottomed flask, then the mixture was heated to 90° C. slowly, and was refluxed under stirring at 90° C. for 0.5 hr. Methanol was added to quench the reaction and Polymer 7 (poly[N,N-bis(4-maleimidophenyl)-N',N'-bis(4-cyanophenyl)-1,4-phenylenediamine]) as brown solid was obtained with a yield of 45% (0.25 g).

Test Example 1 Evaluation of Solubility

N,N-bis(4-maleimidophenyl)-N',N'-bis(4-cyanophenyl)-1,4-phenylenediamine (Compound 6) obtained in Example 1 and poly[N,N-bis(4-maleimidophenyl)-N',N'-bis(4-cyanophenyl)-1,4-phenylenediamine](Polymer 7) obtained in Example 2 were evaluated for their solubility in various solvents by dissolving 2 mg of each in various solvents (2 mL) at room temperature. The results were listed in Table 1.

TABLE 1

| | Solvents | | | | | | | |
|---|---|---|---|---|---|---|---|---|
| Samples | NMP | DMAc | DMF | DMSO | m-Cresol | THF | MeOH | CHCl$_3$ |
| Compound 6 | ++ | ++ | ++ | ++ | ++ | ++ | ± | ++ |
| Polymer 7 | + | + | + | ± | ± | − | − | − |

++: soluble at room temperature
+: soluble under heating
±: partially soluble or swellable under heating
−: insoluble even under heating As shown in Table 1, the pentaphenyldiamine-containing bismaleimide compound, which has a nonlinear and asymmetric structure, has significantly increased solubility in the polar solvent and is soluble in various common organic solvents with low boiling point. Similarly, the polymer formed by polymerization of the bismaleimide also has an asymmetric structure and has better solubility in polar solvents when compared with the conventional polyimide polymers. As shown in Table 1, the polymer is soluble in most of the common polar solvents, which will facilitate its subsequent processing.

The pentaaryldiamine-containing bismaleimide compound of the present invention are readily soluble in various common organic solvents, including those with low boiling point and hence has improved processability; in addition, it has excellent thermostability and may be used as flame retardant or used in improving flame retardancy and heat resistance of other polymers or epoxy resins The above Examples merely illustrate the principles and the effects of the present invention and are not restrictive of the scope of the present invention. Any person skilled in that art can make equivalent modification and alterations on these Examples without departing the spirit and the principle of the present invention and these modifications and alterations should fall within the scope of the appended claims.

What is claimed is:

1. A pentaaryldiamine-containing bismaleimide compound of Formula (I):

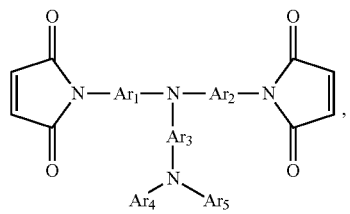

wherein $Ar_1$, $Ar_2$, $Ar_3$, $Ar_4$ and $Ar_5$ are phenyl; and $Ar_4$ and $Ar_5$ are optionally substituted by one or more substitutent(s) selected from the group consisting of $C_1$-$C_6$ alkyl, $C_1$-$C_6$ alkoxy, and cyano.

2. The pentaaryldiamine-containing bismaleimide compound of claim 1, wherein $Ar_4$ and $Ar_5$ are independently substituted by one or more substitutent(s) selected from the group consisting of $C_1$-$C_6$ alkyl, $C_1$-$C_6$ alkoxy and cyano.

3. The pentaaryldiamine-containing bismaleimide compound of claim 2, wherein $Ar_4$ and $Ar_5$ are independently substituted by a cyano group.

4. A method for producing a pentaaryldiamine-containing bismaleimide compound of formula (I),

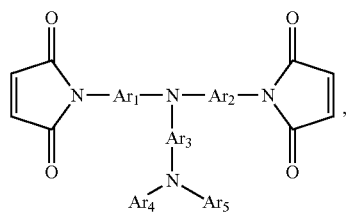

wherein $Ar_1$, $Ar_2$, $Ar_3$, $Ar_4$ and $Ar_5$ are phenyl; and $Ar_4$ and $Ar_5$ are optionally substituted by one or more substitutent(s) selected from the group consisting of $C_1$-$C_6$ alkyl, $C_1$-$C_6$ alkoxy, and cyano, comprising the steps of:

(A) reacting a diamine compound of Formula (II):

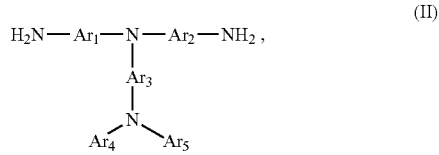

wherein $Ar_1$, $Ar_2$, $Ar_3$, $Ar_4$ and $Ar_5$ are defined as those in Formula (I), with a maleic anhydride of Formula (III):

in a solvent to form a bismaleamic acid; and (B) cyclohydrating the bismaleamic acid obtained in the step (A), in the presence of a catalyst and a dehydrating agent, to form the pentaaryldiamine-containing bismaleimide compound of Formula (I).

5. The method of claim 4, wherein $Ar_4$ and $Ar_5$ are independently substituted by one or more substitutent(s) selected from a group consisting of $C_1$-$C_6$ alkyl, $C_1$-$C_6$ alkoxy and cyano.

6. The method of claim 5, wherein $Ar_4$ and $Ar_5$ are independently substituted by a cyano group.

7. The method of claim 4, wherein the diamine compound is N,N-bis(4-aminophenyl)-N', N'-bis(4-cyanophenyl)-1,4-phenylenediamine.

8. The method of claim 4, wherein the solvent is a ketone solvent or an aprotic polar solvent.

9. The method of claim 8, wherein the ketone solvent is selected from the group consisting of acetone, methyl ethyl ketone, and methyl i-butyl ketone, and wherein the aprotic polar solvent is N,N-dimethylformamide or N,N-dimethylacetamide.

10. The method of claim 4, wherein the catalyst is sodium acetate.

11. The method of claim 4, wherein the dehydrating agent is acetic anhydride.

12. The method of claim 4, wherein the step (A) is carried out at a temperature of −5° C.

13. The method of claim 4, wherein the step (B) is carried out at a temperature of 80° C. to 100° C.

14. The method of claim 4, wherein the molar ratio of the diamine compound to the maleic anhydride in the step (A) is 1:2.0 to 1:2.4.

* * * * *